United States Patent [19]
Conlon et al.

[11] Patent Number: 5,780,302
[45] Date of Patent: Jul. 14, 1998

[54] METHOD OF PACKAGING OXYGEN REFERENCE SOLUTION USING FLEXILE PACKAGE WITH INSIDE VALVE

[75] Inventors: Dennis R. Conlon, South Attleboro; Kevin J. Sullivan, Medfield; Robert B. Green, Hopkinton, all of Mass.

[73] Assignee: Chiron Diagnostics Corporation, E. Walpole, Mass.

[21] Appl. No.: 740,410

[22] Filed: Oct. 29, 1996

Related U.S. Application Data

[60] Provisional application No. 60/006,742 Nov. 2, 1995.

[51] Int. Cl.$^6$ .................................................. G01N 31/00
[52] U.S. Cl. ........................ 436/8; 436/9; 436/11; 436/68; 422/102; 422/103
[58] Field of Search ........................ 436/8, 9, 11, 16, 436/68; 422/99, 100, 102, 103

[56] References Cited

U.S. PATENT DOCUMENTS

| | | | |
|---|---|---|---|
| 3,681,255 | 8/1972 | Wilfore | 436/11 X |
| 4,116,336 | 9/1978 | Sorensen et al. | 436/11 X |
| 4,151,108 | 4/1979 | Sorensen et al. | 436/11 |
| 4,163,734 | 8/1979 | Sorensen et al. | 436/11 |
| 4,289,648 | 9/1981 | Hoskins et al. | 422/83 X |
| 4,470,520 | 9/1984 | Sullivan | 222/94 |
| 4,588,554 | 5/1986 | Kaartinen et al. | 422/61 |
| 4,643,976 | 2/1987 | Hoskins | 436/15 |
| 4,960,808 | 10/1990 | Zowtiak et al. | 436/11 |
| 5,230,427 | 7/1993 | Betts et al. | 206/213.1 |
| 5,405,510 | 4/1995 | Betts et al. | 205/782 |
| 5,421,981 | 6/1995 | Leader et al. | 204/409 |

FOREIGN PATENT DOCUMENTS

| | | |
|---|---|---|
| 0518191 | 12/1992 | European Pat. Off. . |
| 0520443 | 12/1992 | European Pat. Off. . |

*Primary Examiner*—Maureen M. Wallenhorst
*Attorney, Agent, or Firm*—Arthur S. Morgenstern; Charles L. Gagnebin, III; Robert P. Blackburn

[57] ABSTRACT

A novel flexible package for an oxygen reference solution has been developed. This package is made from a laminated film including preferably polypropylene as the inner layer, aluminum foil as the middle layer, and polyester as the outer layer. The seams are heat sealed, while an optional access device for allowing access to the solution after the storage period, is attached to the inside wall of the bag without breeching the middle barrier layer.

13 Claims, 4 Drawing Sheets

METHOD OF PACKAGING OXYGEN REFERENCE SOLUTION USING FLEXILE PACKAGE WITH INSIDE VALVE

This application claims the benefit of U.S. provisional application Ser. No. 60/006,742, filed Nov. 2, 1995.

BACKGROUND OF THE INVENTION

In clinical chemistry analyses, it is important for the clinical chemist or instrument operator to have reference solutions to calibrate the analyses being conducted or the analyzer and to determine whether the assays produce reliable results. One type of these reference solutions is a calibrator, which, when run in the assay, is used to set the response level of the sensors. A control, on the other hand, is a solution having a known concentration of an analyte or analytes contained in the same, or similar, matrix in which the samples to be analyzed exist. The assay results from the control product are compared to the expected assay results to assure that the assay technique is performing as expected.

Commercial blood gas analysis systems have been available since the 1960's. The earliest reference materials were gas mixtures in pressurized cylinders, and these are still the most commonly-used. In the 1970's, the development of liquid reference solutions began, leading to products in which reagents have been equilibrated with precision gas mixtures and packaged in flexible containers with zero headspace, usually requiring refrigeration to maintain stability or resorting to calculations to compensate for gas content changes during storage.

Most quality control materials for these analyzers consist of tonometered aqueous solutions (a solution containing dissolved gases) in glass ampules. The typical gas headspace above the liquid in these ampules provides a reserve of oxygen against any potential oxygen-consuming reactions which may occur within the solution during the shelf life of the product.

In the absence of a gas headspace within their containers, reference solutions for oxygen determinations are particularly difficult to make and maintain stable. First, the instability may be due to reactivity between the dissolved oxygen and the other components of the calibrator. The other components of the calibrator might either react with the dissolved oxygen, reducing its concentration, or, alternatively, the other components may react with each other to generate oxygen, thus also changing the oxygen concentration. Second, the solution might be contaminated with microorganisms which, due to their metabolism, might change the oxygen content. Third, the oxygen might permeate through, or react with, the packaging material, also affecting the oxygen content of the reference material.

Reference materials that are manufactured for distribution in commerce must be made to withstand the various conditions encountered in the distribution chain and must be sufficiently stable to provide good performance within the time frame in which they are expected to be used by the customer, which is approximately 1 year for the typical calibrating solution distributed to commercial laboratories and hospitals. In addition, reference solutions, as with other reagents, should be packaged in containers which are easy to handle, convenient to use and which meet other design requirements of their intended usage. This is particularly true of reagents which are used in conjunction with various analytical instruments.

The users of instruments which determine the oxygen partial pressure of blood and other body fluids have a need for the above calibration materials and would benefit from oxygen reference solutions over the more conventional precision gas mixtures in cylinders with regulators, because they allow for simultaneous calibration of gas and non-gas sensors. In addition, they are inherently less expensive, safer, and easier to manipluate than high-pressure gas tanks. Although oxygen calibration solutions have been made in the past, they have suffered from being unstable and having expensive, complicated, or unreliable means to access their contents. Some calibrators, when used on assay instruments, have extended their usefulness by allowing the instrument to calculate the expected oxygen level, said level being calculable from the age of the product, given the fact that the rate of decrease in oxygen level can be predicted based on historic performance. Several developers have included inner layers of plastic materials selected because of their heat sealability (U.S. Pat. No. 5,405,510—Betts) or low gas permeability (U.S. Pat. No. 4,116,336—Sorensen) or gas tightness (U.S. Pat. No. 4,163,734—Sorensen). Some have disclosed that the inner layer should be inert, but have not provided enablement as to how to select such an inner layer (U.S. Pat. No. 4,643,976—Hoskins) and/or weren't capable of maintaining oxygen at a precise level appropriate for blood gas purposes.

An additional shortcoming of previous oxygen calibration liquid storage devices has been the opening or valve required to access the fluid for use, while maintaining the integrity of the fluid during storage. The materials available for valve construction and the need to breech the barrier layer to incorporate the valve have compromised fluid stability.

SUMMARY OF THE INVENTION

A novel flexible package for an oxygen reference solution has been developed. This package is made from a laminated film comprising preferably polypropylene as the inner layer, aluminum foil as the middle layer, and polyester as the outer layer. The seams are heat sealed, while an optional access device for allowing access to the solution after the storage period, is attached to the inside wall of the bag without breeching the middle barrier layer.

BRIEF DESCRIPTION OF THE DRAWINGS

FIG. 1b is a cross-sectional side view of the package of FIG. 1a;

FIG. 1c is a first end view of the package of FIG. 1a;

FIG. 1d is a second end view of the package of FIG. 1a;

FIG. 4a is a top view of the device of FIG. 4a;

FIG. 4b is a side view of the device of FIG. 4a; and

DETAILED DESCRIPTION OF THE INVENTION

Figure 1A:
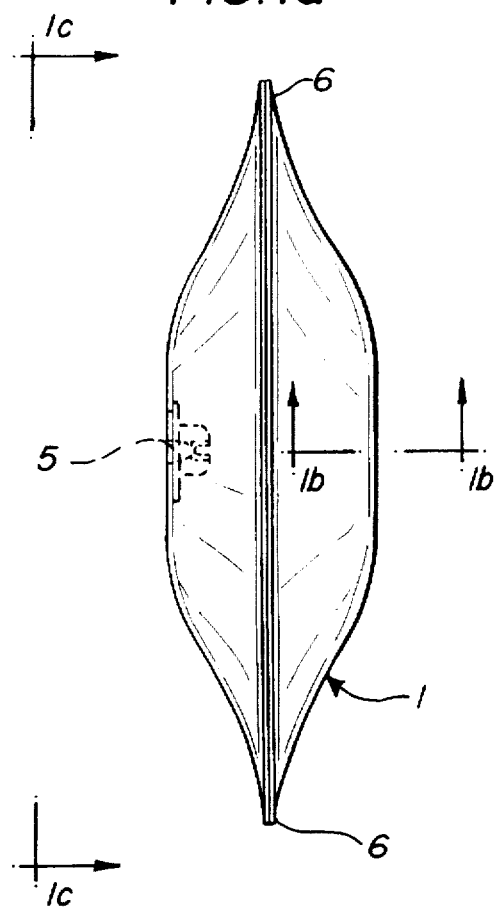
FIG. 1a is a side view of a multilayer package used in the method of the present invention.
Figure 1B:
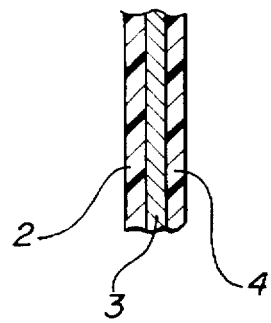

A novel flexible package for an oxygen reference solution has been developed. Typical oxygen reference solutions comprise sodium, potassium, and calcium chloride salts, pH buffer, sodium bicarbonate, calcium chelating agent, surfactant, and biocide, which are equilibrated under partial vacuum with a carbon dioxide/oxygen gas mixture before filling. The typical oxygen partial pressures are from about 40 up to about 400 mmHg, but partial pressures as high as 2000 mmHg (i.e., greater than ambient) can be used, as well as partial pressures as low as zero (no oxygen present). This package stabilizes the oxygen reference via the use of a multilayered film as the packaging material. In addition, the package incorporates an unusual access device for removing the solution. The device, which is called an access device, is not exposed to the outside of the container. Instead it is sealed within the container and, as a result, does not provide an opportunity for there to be leakage around the seal during the pre-use storage as opposed to having the access device sealed within the package seam or through the wall of the container, where one would ordinarily expect it to be sealed.

FILM

The film which is used for the container is multilayered and preferably utilizes polypropylene (PP) for the inner layer, aluminum foil for the middle layer, and polyester for the outer layer. The outer layer merely provides protection for the aluminum layer, preventing abrasion and corrosion. Thus, for example, a nylon layer or even a simple lacquer coating are suitable alternatives. An important parameter of the aluminum layer is that it be thick enough so that there are no pinholes, thus preventing physical leakage of oxygen, yet thin enough so that it can be readily formed into pouches on automated machines and will, after being filled, release its contents without undo force by readily collapsing as the contents are removed.

The inner PP layer is important for several reasons. First, it must melt and form the seal which closes the package. Second, it must be unreactive with the oxygen. It is this second factor which distinguishes this packaging material from those previously used for this purpose. This laminate has never been used commercially for packaging products which contain high-precision solutions with dissolved gases for scientific, medical, analytical purposes. The PP lined laminate is not known to be used by others as an oxygen barrier for chemical products. One other manufacturer of oxygen calibrators (Mallinckrodt Sensor Systems, Inc., Ann Arbor, Mich.) uses laminated film to package a calibrator, but they seem to use polyethylene as the inner, sealing layer. The PP lined laminate has been used in the past mainly for food products, and has been chosen for the high melting point of the polypropylene sealing layer, which makes this material suitable for sterilization in a steam autoclave or similar equipment.

Films from various suppliers were evaluated for efficacy in maintaining the dissolved gas concentrations of solutions stored within. Films were obtained from Kapak Corp., Minneapolis, Minn. (part no. 50703), American National Can Co., Mount Vernon, Ohio (part nos. M-8309, M-8359, M-8360), James River Corp., Cincinnati, Ohio (part nos. JR 4123, JR 4400), Technipaq, Inc., Crystal Lake, Ill. ("Dull Foil Laminate"), Lawson Mardon Flexible, Inc., Shelbyville, Ky. (spec nos. 13362 and 15392), Smurfit Flexible Packaging, Schaumburg, Ill. (LC Flex 70459, 70464), and Rollprint Packaging Products, Inc., Addison, Ill. (RPP #26-1045). 4-sided bags were either purchased with 3 sides pre-sealed or were formed using an impulse heat sealer from Toss Machine Components, Inc., Bethlehem, Pa., Model 01617. The 3-side sealed bags were filled with various reference solutions and immediately sealed through the liquid, allowing no headspace inside the package. In some instances, for enhanced stability of the oxygen partial pressure in the reference solution stored within the bags, filled, sealed bags were heat-treated at elevated temperatures between approximately 50° C. and 121° C. for times ranging from 15 minutes to 7 days, depending on the temperature.

A typical bag is shown in FIG. 1a where view (a) shows a side view of a sealed bag 1, and one possible location of the access device 5 in the interior of the bag is shown. The sealed portion of the bag is also shown 6. View (b) shows the 3 layers of the film, the inner polypropylene layer 2, the middle aluminum layer 3, and the outer polyester layer 4.

Some filled bags were left at room temperature; others were stored at elevated temperatures for various times. To simplify reporting of this and subsequent trials, we used storage at 55° C. for 1 week as a basis for comparison. After removing test bags from the incubator, they were cooled to room temperature and tested on two critical care analyzers (generally selected from the 200 series manufactured by Ciba Corning Diagnostics Corp.; a 278 was often used with a 288) with control bags in the same run. In particular, the pO2 results were examined in a series of six studies. Due to differences in conditions such as reagent composition and package surface-to-volume ratios, the $pO_2$ differences are not directly comparable. Therefore, all results were converted to relative scores where the most stable laminate was assigned a score of 1.00 and all other laminates were assigned scores on the basis of $\Delta pO_2$ ratios. Using this convention, the following results were obtained:

TABLE I

| Material | N | Mean Score | Range of Scores |
|---|---|---|---|
| Polyethylene | 4 | 0.14 | 0.10–0.16 |
| Polypropylene | 6 | 0.41 | 0.18–1.00 |
| Polyester | 2 | 0.28 | 0.26–0.30 |

The preferred and most preferred laminates have an inner PP liner of the thickness shown below, a middle layer of aluminum as shown below, and an outer polyester layer. (The thickness and material selection of the outer layer is least critical and can vary somewhat.) Acceptable film thicknesses are also shown.

Approximate thicknesses of layers in mils (1/1000 inch):

TABLE II

|  | Polypropylene | Aluminum | Polyester |
|---|---|---|---|
| Most preferred | 4 mil | 0.5 mil | 0.5 mil |
| Preferred | 2–5 mil | 0.5–0.7 mil | 0.5 mil |
| Acceptable | 1.5–5 mil | 0.3–1.0 mil | 0.2–2 mil |

Other acceptable layers include polyester at 0.5–2 mil for the inner layer; for the outer layer either nylon with thickness of 0.2–2 mil or lacquer coating. Polyethylene has not been found to be acceptable as an inner layer.

Note that the thickness of the PP layer is outside of the range of that referred to in Betts and Sorensen. In addition, the enablement in Betts was limited to selection of an inner layer based on its sealability; no mention was made of the attribute of non-reactivity. Furthermore, the item packaged by Betts was a sensor, for which the loss of oxygen was not critical during the transport period, thus being a case where significant change in oxygen concentration was tolerable. It was only important to Betts that the sensor remained moist.

There are detrimental properties that result if any of the film layers are too thick. Namely, the laminate becomes too rigid, making it difficult to form and fill during manufacture, and difficult to pump out the liquid contents from the pouch/bag during use. Furthermore, if the aluminum layer is too thin, there is a higher probability of having pinholes, which may lead to gas leakage. If the sealing layer is too thin, it may be entirely displaced at the moment of heat-sealing at the seal under the 40+ PSI pressure required for strong seals, thereby exposing bare aluminum which would react with oxygen.

Stability testing has shown that the PP lined film is preferred over the polyethylene film. The Arrhenius method of predicting product shelflife is well-established in the in-vitro diagnostics and pharmaceutical industries (Conners et al, "Chemical Stability of Pharmaceuticals: A Handbook for Pharmacists", N.Y.: Wiley, 1986; Porterfield & Capone, MD&DI 45–50, April 1984; Anderson & Scott, Clin Chem 37:3, 398–402, 1991; Kirkwood, Biometrics 33, 736–742, December 1977). Products are stored at elevated temperatures for various times, following which they are re-equilibrated at ambient temperature and tested against non-stressed controls for critical properties such as activity of a component or measured analyte. The rate of change or more conveniently, the time-to-failure, of a given analyte is determined for each temperature, often by plotting log(C/Co) vs time, which is a linear function for the most common, first-order, reactions. Owing to the linear relationship between log(time-to-failure) and the inverse of the absolute temperature (1/K), a plot can be constructed from the elevated-temperature data, and the resulting line can be extended to the maximum recommended storage temperature to predict the time-to-failure at that temperature. In this manner, actual shelflife can be predicted in advance.

In an early predicted shelflife study using polyethylene-lined bags, finished packages were stored at 35°, 45°, and 55° C. for times ranging from 4 days to 8 weeks, depending on the storage temperature, using longer times with lower storage temperatures. Each test condition included 4 bags tested on two blood gas analyzers (CCD, 200-series). Time-to-failure (TTF) was defined as a 2% change in $pO_2$.

TABLE III

| Temperature | 1/K | Time-to-Failure | Log(ttf) |
|---|---|---|---|
| 55° C. | .0030488 | 0.6 weeks | −0.222 |
| 45 | .0031447 | 1.1 | 0.036 |
| 35 | .0032468 | 4.4 | 0.647 |

Regression analysis on the above data, based on plotting log(ttf) as a function of 1/K, results in a predicted 25° C. shelflife of 3 months. The correlation coefficient, r, is 0.98.

In the polypropylene study, finished packages were stored at 35°, 40°, 45°, and 50° C. for times ranging from 1 to 9 weeks, depending on the storage temperature, using longer times with lower temperatures. Each test condition included 3 bags tested in singlicate on two blood gas analyzers (CCD, 200-series). The first-order model was used to determine time-to-failure (TTFs), where failure was defined as a 2% change in pO2.

TABLE IV

| Temperature | 1/K | Time-to-Failure | Log(ttf) |
|---|---|---|---|
| 50° C. | .0030960 | 1.3 weeks | 0.106 |
| 45 | .0031447 | 3.3 | 0.521 |
| 40 | .0031949 | 5.7 | 0.755 |
| 35 | .0032468 | 12.3 | 1.091 |

Figure 5:
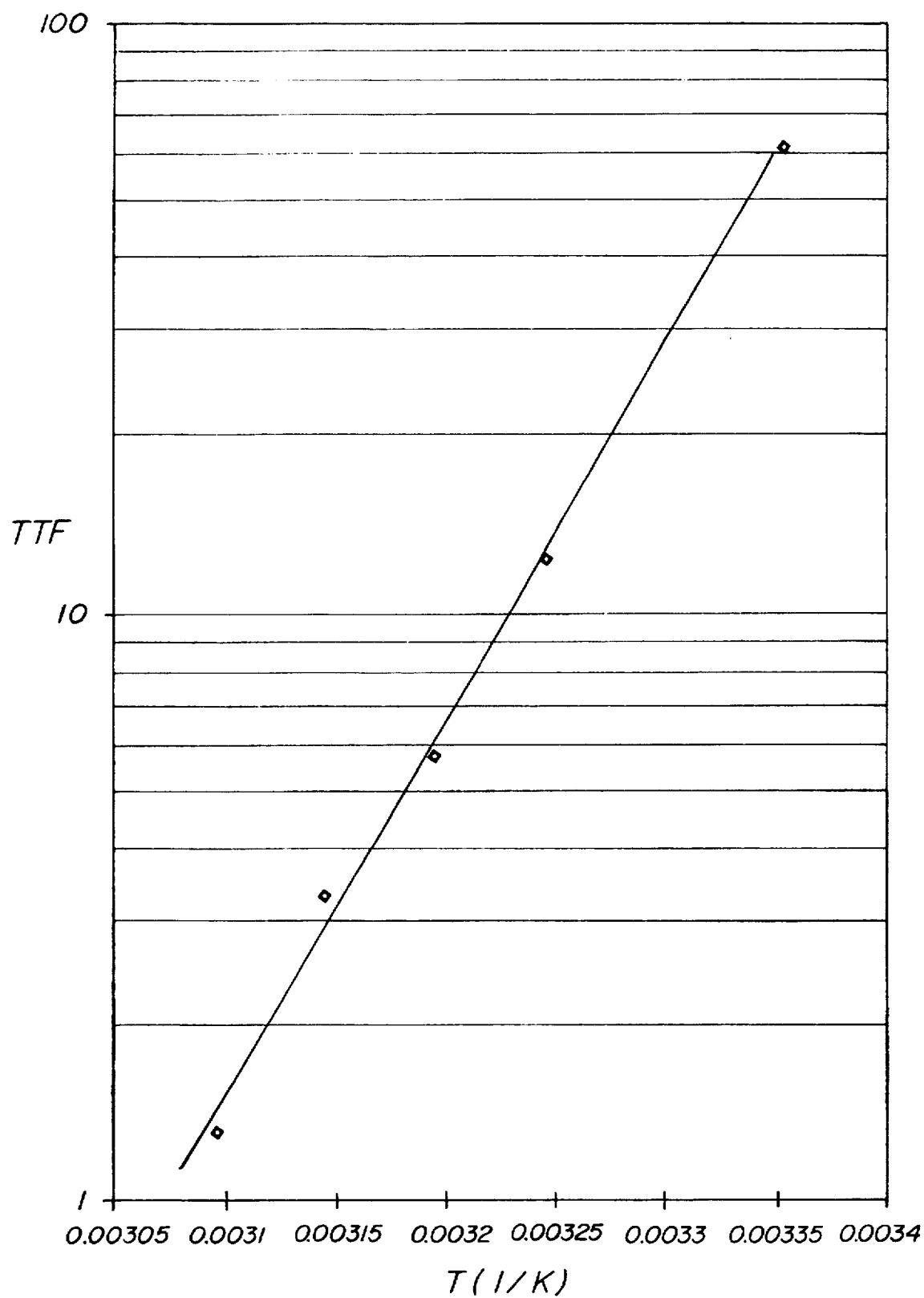
FIG. 5 is an Arrhenius diagram showing the predicted shelf life of a typical formulation using the method of the present invention.

Using the four TTFs, an Arrhenius plot was constructed (See FIG. 5), where time to failure (in weeks) (TTF) is shown as a function of inverse temperature, 1/K (shown as T in FIG. 5). (1/K is the inverse of Kelvin temperature.) The linear extrapolation to 25° C. is 61 weeks or 14 months, for an average pO2 change of −0.066 mmHg/wk. The reliability of the prediction is affirmed by the highly linear relationship among the 4 points, with a correlation coefficient, r, of 0.99. A score of 1.00 would indicate that all points fall on a straight line; a score of 0.00, that no relationship exists between log ttf and 1/K. (Note that the equation for the Arrhenium plot exemplified was found to be log y=−19.48+ 6339x.)

The resulting predicted shelflife represents a four-to-fivefold improvement over the shelflife predicted for oxygen reference solution stored in the polyethylene-lined bags. It also represents nearly tenfold improvement over the current state of the art product, which is known as "Cal B" from Mallinckrodt Sensor Systems, Inc., Ann Arbor, Mich. The software in the GEM® Premier Analyzer sold by Mallinckrodt automatically subtracts 0.58 mmHg pO2 from the initial assigned pO2 for every week which has elapsed since manufacturing in order for the Cal B calibrator to be useable for its expected commercial usage period. If not for this calculation, using our 2% criterion, the useful shelflife would be only 7 weeks, clearly too short a time for commercial use of the product. Moreover, note that their actual Cal B shelflife, 6 months, limits the shelflife of the entire cartridge to only six months, arguably the minimum practical shelflife for an in-vitro diagnostic product. On the other hand, 14 months is clearly an acceptable shelflife.

PP-lined laminates are also more expensive than those made from polyethylene. If purchased as 3-side-sealed bags, the following comparison can be made:

Custom Polyethylene-lined from Technipaq, 3.5×7"= $0.24/bag in lots of 1000

Stock Polyethylene-lined from Technipaq, 4×5"=0.11

Custom Polypropylene-lined from Kapak, 3.5×11.5"= $0.69/bag in lots of 1000

Stock Polypropylene-lined from Kapak, 5×8"=0.40

Even though this comparison is confounded by including different vendors and different bag sizes, it is clear that the PP-lined laminates, which tend to have a thicker sealing layer, cost at least double compared with PE-lined laminates. The greater cost of the PP-lined laminates is one reason why they are less common than the PE-lined laminates.

Other factors which discourage use of PP-lined laminates are their greater stiffness and higher melting points. PP durometer hardness, on the Shore D scale (ASTM Designation: D 2240-91 American Society for Testing and Materials, Philadelphia, Pa.), is 70–80 compared with only 44–48 for PE. Stiffness impedes high surface:volume ratio, which improves shelflife, and makes automation on form/ fill/seal machines more difficult. The higher melting point for PP, 171° C. compared to only 137.5° C. for PE, requires more energy, time, or both to seal the bags.

THE ACCESS DEVICE

The access device is attached inside of the pouch. Attachment can be achieved using any technique available, for example, via use of adhesive, heat-bonding, ultrasonic welding, etc. This access device is an optional component of the package and is particularly useful when the contents of the container are used over a period of time after a prolonged storage interval. In previous approaches, a valve has been sealed into the edge or through the wall of the container so that it would be accessible from the outside of the container. However, in the package used herein, the access device is sealed totally within the package on the inner wall, and does not breach the seal or the walls of the container.

Figure 2:
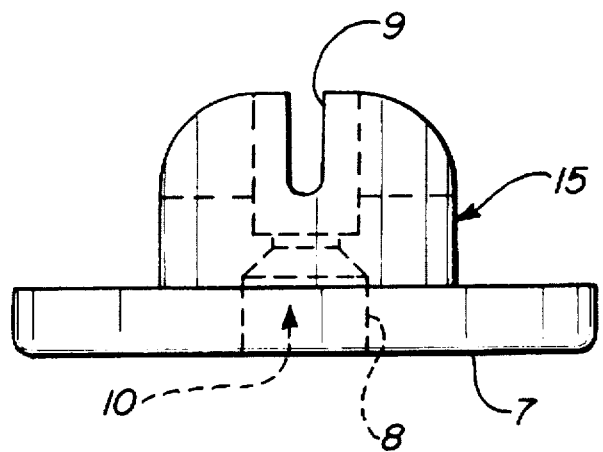
FIG. 2 is a side view of an access device utilized in the method of the present invention.
Figure 3:
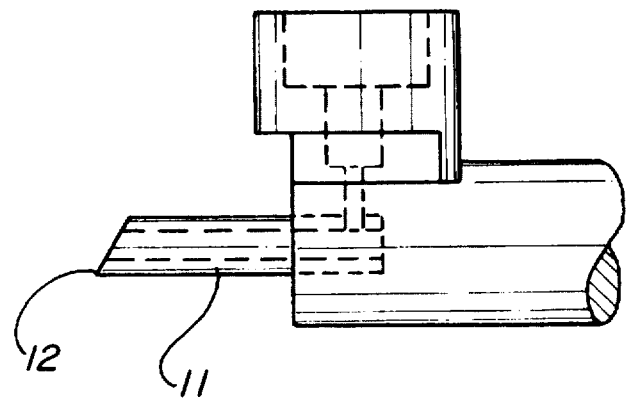
FIG. 3 is a side view of a probe which mates wit the access device of FIG. 2.
Figure 4:
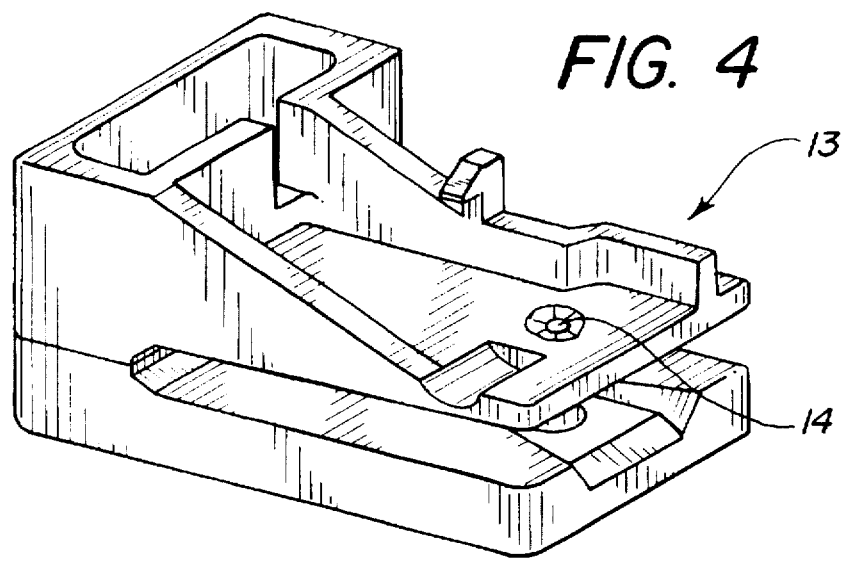
FIG. 4 is a diagram of a clamp and locating device used with the method of he present invention.
Figure 4A:
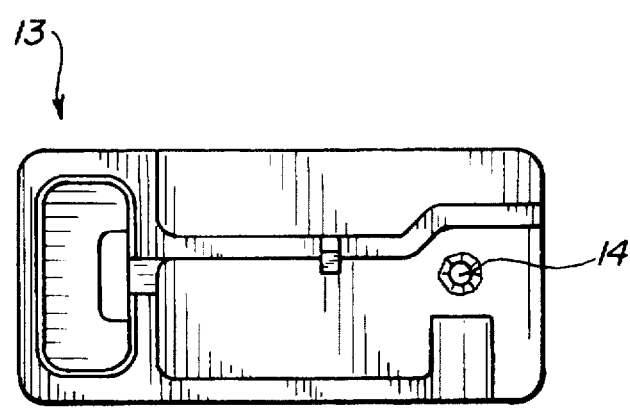
Figure 4B:
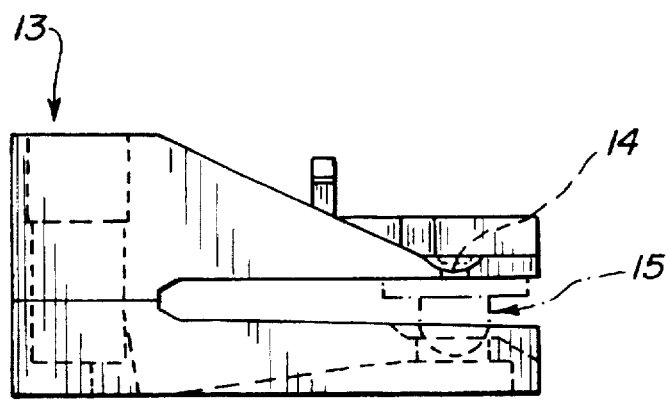

FIG. 1a shows a typical location for the access device. FIG. 2 shows the detail of a typical access device, with 7 being the portion of the access device sealed to the wall of the container, 8 being the outer portion of the delivery channel, 9 being the inner portion of the delivery channel, and 10 being the sealed portion of the delivery channel which is punctured by the probe, which then makes a tight fit with the inner portion of the delivery channel, thus preventing leakage from the container. FIG. 3 shows a typical probe, which is used to puncture the bag and the access device inside the bag, with 11 representing the probe and 12 representing the sharp end of the probe which punctures the sealed portion of the delivery channel. The probe is incorporated in a clamping device 13 (see FIGS. 4–4b) which has a circular opening 14 which fits over the hemispherical back of the access device 15 aligning the probe with the delivery channel. The probe is connected to other components which allow the calibrating solution to flow to the apparatus where it can be utilized in assays. When the package is punctured, the probe pierces the wall and forms a tight seal with the delivery channel of the access device. Before the package is punctured the access device is totally isolated within the (more or less) impermeable walls of the container. This approach has an advantage over other valves and access devices in that it does not provide a diffusion pathway to the outside environment. Obviously there can be variations in the design of the access device and probe, which will be apparent to those with skill in the art.

The access device is also made of PP so that it seals well with the wall of the container. The description of the access device should allow for some variations of the preferred access device. For example, the access device might be sealed to both walls of the package to provide an added benefit of stabilizing the shape of the package. The access device can be sealed at any location inside the container, for example, in a corner (for ease of attaching a clamp) or away from the edge of the container. Furthermore, the access device does not need to be attached to the container if there is some technique incorporated for locating the access device. For example, if the access device were to contain an embedded magnet, the application of an exterior magnet could be used to capture and position the access device. Other shapes (cones, indents, etc.) might be used for the locating feature. Rings can be molded into the inner wall of the delivery channel to improve the seal after puncture. The travel distance of the probe can be limited to prevent puncture of the adjacent wall of the container.

REACTIVITY OF OXYGEN WITH POLYPROPYLENE

The oxygen is much less reactive with PP than it is with polyethylene. It is this lower reactivity that makes PP a more desirable material to be used as an inner layer. In the past, developers were concerned with permeability of the inner layer to oxygen, but this turns out, however, to be a less important attribute than the reactivity for this type of reference solution.

Both PP and polyethylene provide reasonable sealing, although the PP has a higher melting temperature. In addition, both materials provide equivalent leak protection. However, in polyethylene, there is more reactivity between oxygen and the polymer, thus reducing the oxygen level. It is not permeation through the polyethylene film that was largely responsible for reducing the oxygen level. This argument is based on the following:

1. Although the $pO_2$ level in the oxygen reference solution seems to be considerable, at roughly 200 mmHg, in molar terms, it is only 0.27 mmol/L. The calculation to convert from mm Hg partial pressure to mmol/L oxygen concentration is reasonably simple and straightforward, but oxygen is rarely described in the literature in molar units. Rather, where it is not in partial pressure units such as mm Hg or kPa, it is found in concentration units such as mg/L or mL/dL. However, approaching the oxygen loss problem from the molar perspective teaches us that reaction of only 0.005 mmol/L (2%) would cause product failure. Ultraviolet (UV) spectroscopy studies showed that at elevated temperatures, water-soluble, UV-absorbing substances are extracted from the sealing layer into the bag contents. This is true for both PP- and PE-lined bags. Finally, whereas only 0.005 mmol/L reactant is required for product failure (by $pO_2$ decrease), with 100 mL reagent in a 4"×6" bag, only 0.1% of an additive with a molecular weight of 500 in a 4 mil PP film would provide 0.05 mmol/L of oxidizable reactant, ten times the amount needed to explain a 2% decline in $pO_2$. Thus, the stoichiometry is reasonable, even assuming an extraction efficiency of only 10%.

2. PP sealing layers from different vendors differ markedly in the $pO_2$ changes in oxygen calibrator sealed within them when they are subjected to elevated temperatures, as demonstrated in Table I above. Yet the permeability of polypropylene roll stock from any of the several vendors can be expected to be similar because it should be a property of the bulk polymer, unless it has been modified into an oriented polypropylene. (Oriented PP is not known to be laminated to aluminum foil.) Thus, it is unlikely that permeability differences can explain the differences in $pO_2$ deltas shown in Table I. However, since the various PP vendors are known to use a considerable variety of additives to the basic PP resin (these additives being nearly always proprietary), it is quite likely that differences in additives among the various resins explain a considerable portion of the differences in $pO_2$ deltas, as different additives or even the same additives in different concentrations would react to a greater or lesser degree with the oxygen in the calibrator.

3. The most convincing evidence to support the importance of reactivity over permeability is from an experiment which isolated the two effects. A uniform population of 3-side-sealed bags were filled with an oxygen calibration solution tonometered such that oxygen partial pressure would be roughly 200 mmHg. A control group of bags was filled normally and immediately sealed on the Toss impulse sealer. Two test groups had five pieces, cut so as to just fit into the bag, of either polyethylene or polypropylene added to the bags just before filling and sealing. As in the stability tests described above, some bags from all three groups were left at room temperature, while others, randomly selected, were stored at 55° C. for 1,2, and 3 weeks. Bags were cooled to and allowed to equilibrate at room temperature for at least 24 hours, and then tested in the usual manner, that is, in triplicate on two 200-series blood gas analyzers (Ciba Coming, Medfield, Mass.), alternating during runs between control and test conditions. The following results were obtained:

| Test Group | Stress Condition | $pO_2$, mean (SD) | $\Delta pO_2$ | Net $\Delta pO_2$ |
| --- | --- | --- | --- | --- |
| Control | Control | 201(3) mmHg | –10 mmHg | |
| | 3 wks at 55° C. | 191(1) | | |
| + Polypropylene | Control | 219(3) | –13 | –3 mmHg |
| | 3 wks at 55° C. | 206(6) | | |

-continued

| Test Group | Stress Condition | pO$_2$, mean (SD) | ΔpO$_2$ | Net ΔpO$_2$ |
|---|---|---|---|---|
| +Poly-ethylene | Control 3 wks at 55° C. | 221(2) 179(6) | −42 | −32 |

The effect of the polyethylene on pO$_2$ is both dramatic, being an order of magnitude more severe than polypropylene, and significant, with the additional 29 mmHg decrease being nearly five times the greatest SD, 6 mmHg. Permeability cannot explain this difference because the plastic sheets were contained entirely within the bags.

The package described herein is novel. First, the packaging material was selected because of the non-reactivity of its inner layer with oxygen. Second, the thickness of its layers are different from those of previous flexible packages. Third, the package described herein has an optional, novel valve or access device, which reduces the amount of leakage and better maintains the integrity of the contents of the container. Fourth, all prior art in this area of technology was based on 4-sided bags with the security of one continuous seal around the entire perimeter of the package; whereas we disclose a 3-sided, center-seal pouch having in places two, in other places four, layers of laminate to seal through, and six stress points per bag where laminate is folded at 360° and where one might therefore expect that a thin channel allowing gas exchange might result.

Although Betts disclosed a polymer foil laminate material which has an inner layer which is heat sealable, polypropylene is identified as a possible inner layer because of its sealability (see cols. 14–15 therein). In addition, it discusses the gas impermeability of the bags (col 14, line 34ff) as the attribute of value. Also, the inner layer described in Betts is 0.1 to 1¼ mil, much thinner than the layer herein. The layers are described (col 14, line 62ff and col 15, lines 1,2) in weight per area units, that is, grams per meter$^2$. These units were converted into the more common mil thickness units based on the following densities:

| Material | Density |
|---|---|
| Polyvinylidene Chloride | 1.7 g/cc |
| Polyester | 1.3 |
| Nylon | 1.1 |
| Polyethylene | 0.9 |
| Polypropylene | 0.9 |

Figure 1D:
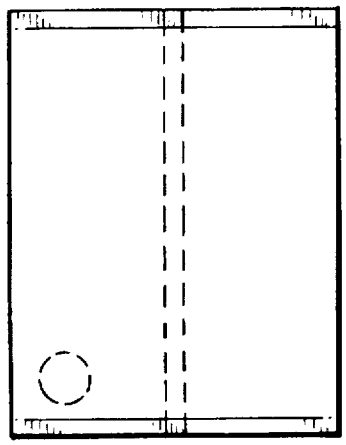
Figure 1C:
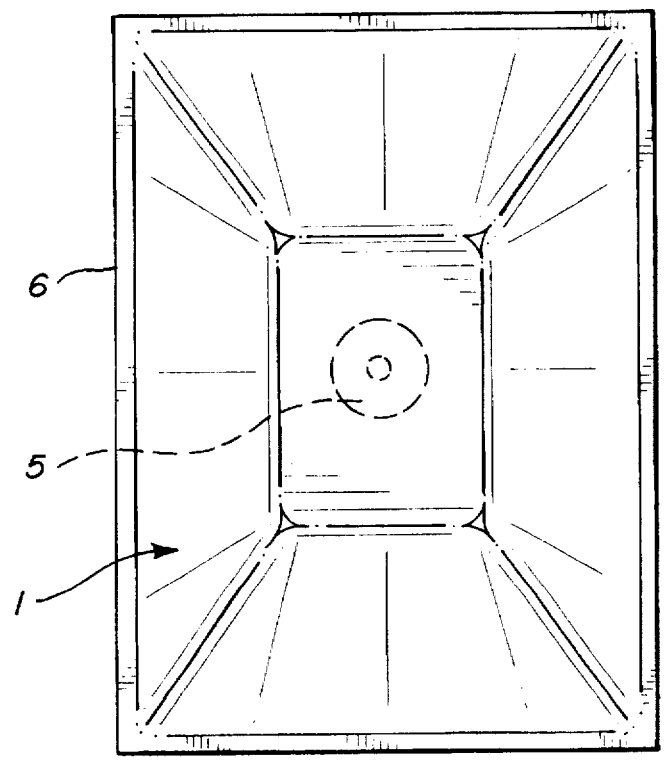

Thus, for the critical inner layer, variously described as 5 to 25 g/m$^2$ and 45 g/m$^2$, the minimum thickness is based on 5 g of polyvinylidene chloride, for a thickness of 0.1 mil, while the maximum thickness is based on 45 g of polypropylene, for a thickness of 1¼ mil.
The latter calculation is shown below:

(45 g/sq.m)/(0.9 g/cc)=50 cc/sq m=50 cc/sq cm×10$^{-4}$=50 cm×10$^{-4}$= 50 microns Other variations on the packaging method are possible. For example, other shapes of packages that reduce the ratio of surface area of package to volume of solution and gas within the package (e.g., 2 circular pieces of film which are sealed together), would reduce even further the exposure of the solution and gas to the film, even further reducing the oxygen degradation. The packaging disclosed herein is also effective in protecting tonometered solutions containing other gases aside from oxygen. Furthermore, various configurations of package (e.g., three-sided seal or side-seam; four-sided sealed; gusseted packages; or "stand-up" pouches) can be used. (Compare, for example, FIG. 1c, which shows 4 sides sealed, to FIG. 1d, which shows a 3-sided seal.) These package variations affect utility of the packaging method and are not simply design alternatives. Other variations will be apparent to those with expertise in this technology area.

We claim:

1. A method of maintaining the stability of an oxygen reference solution comprising the step of:

packaging an oxygen reference solution in a package comprising:

multiple laminated layers, said laminated layers comprising:

an inner layer of a heat-sealable polymer film;

a middle layer of aluminum; and an outer layer selected from the group consisting of polyester nylon and a lacquer coating; and an access device disposed completely within said package in contact with said oxygen reference solution wherein said access device does not breach said multiple laminated layers and wherein said access device allows access to the oxygen reference solution in the package while maintaining the integrity of the solution during storage and preventing exposure of the solution to the outside environment when the access device is punctured by a probe.

2. A method of claim 1 in which said heat-sealable polymer film is selected from the group consisting of polypropylene and polyester.

3. A method of claim 1 in which said inner layer has a thickness approximately between 1.5 mil and 5 mil, said middle layer has a thickness approximately between 0.3 mil and 1 mil, and said outer layer has a thickness of approximately 0.2 mil to 2 mil.

4. A method of claim 1 in which said inner layer has a thickness of about 2–5 mil, said middle layer has a thickness of about 0.5–0.7 mil, and said outer layer has a thickness of about 0.5 mil.

5. A method of claim 1 in which said inner layer has a thickness of about 4 mil, said middle layer has a thickness of about 0.5 mil, and said outer layer has a thickness of about 0.5 mil.

6. A method of claim 1 in which said oxygen reference solution comprises a known, stable level of oxygen.

7. A method of claim 6 in which the oxygen reference solution contains a known, stable level of glucose.

8. A method of claim 6 in which said oxygen reference solution also comprises other metabolites.

9. A method of claim 8 in which said metabolites are selected from the group consisting of lactate and urea.

10. A method of claim 1 in which said access device is connected to one or more walls of said package.

11. A method of claim 10 in which said package is formed into a 3-side, center-sealed pouch.

12. A method of claim 1 in which said access device is made of polypropylene.

13. A method of claim 1 in which said access device is not connected to a surface of the package.

* * * * *